United States Patent [19]

Schomburg et al.

[11] Patent Number: 5,141,612
[45] Date of Patent: Aug. 25, 1992

[54] PRODUCTION OF POLYACRYAMIDE GEL FILLED CAPILLARIES FOR CAPILLARY GEL ELECTROPHORESIS

[75] Inventors: Gerhard Schomburg; Jürgen A. Lux; Hong-Feng Yin, all of Muml/u/lheim/Ruhr, Fed. Rep. of Germany

[73] Assignee: Studiengesellschaft Kohle MBH, Mulheim/Ruhr, Fed. Rep. of Germany

[21] Appl. No.: 626,603

[22] Filed: Dec. 12, 1990

[51] Int. Cl.$^5$ .................... C25B 1/00; C25B 7/00; B01D 61/42
[52] U.S. Cl. .................... 204/182.8; 204/299 R; 204/180.1
[58] Field of Search .................... 204/182.8, 299 R

[56] References Cited

U.S. PATENT DOCUMENTS 4,680,201  7/1987  Hjerten .................... 204/182.8
4,865,707  9/1989  Karger .................... 204/182.8

Primary Examiner—John Niebling
Assistant Examiner—Caroline Koestner
Attorney, Agent, or Firm—Sprung Horn Kramer & Woods

[57] ABSTRACT

Polyacrylamide gel filled silica capillaries of improved performance in electrophoresis are produced by
 a) leaching the capillary with a solution of a basic reagent;
 b) binding a substituted, double bond-containing silane to the silica surface of the capillary;
 c) binding an acrylamide to the treated surface and polymerizing the acrylamide to a linear polyacrylamide, eliminating electroosmotic flow and avoiding chemical bonding of the gel during its subsequent formation; and
 d) contacting the capillary with a solution of acrylamide/bisacrylamide and effecting crosslinking polymerization in the presence of a radical polymerization starter to form a gel.

5 Claims, 6 Drawing Sheets

A  Gels free of bubbles are obtained without surface pretreatment.

B  Equidistant bubbles are generated when surface is pretreated with 3-methacryloxypropyltrimethoxysilane.

A Gels free of bubbles are obtained without surface pretreatment.

B Equidistant bubbles are generated when surface is pretreated with 3-methacryloxypropyltrimethoxysilane.

PRODUCTION OF POLYACRYAMIDE GEL FILLED CAPILLARIES FOR CAPILLARY GEL ELECTROPHORESIS

BACKGROUND OF THE INVENTION

The invention relates to the provision of polyacrylamide gel filled capillaries for electrophoresis of improved performance and suitably are provided by using a special process of production. After special steps of surface pretreatment the gels polymerized in such capillaries are stable for long series of routine separations. The formation of bubbles during the formation of the gel within the capillary is avoided. Such bubbles affect the usefulness of the capillaries. Separations of various oligonucleotide samples illustrate the performance of the novel gel capillaries. The symmetry of peaks as achieved in such separations is superior to that obtained without the novel surface pretreatment.

For analytical applications, the classical electrophoretic separations using slab gels have certain advantages in comparison to gel capillaries. Several samples can be separated side by side simultaneously and with the same separation parameters. Such parallel separations allow accurate matching of the position of individual components in the eltropherogram on the slab which may originate from different samples. Separations in gel capillaries can be performed with higher resolution or speed of analysis, however.

Therefore and for other reasons the further miniaturization of gel electrophoretic systems has gained in interest, recently. Capillaries with small internal diameters are characterized by a larger surface-area-to-volume ratio, which is of advantage for better dissipation of Joule heat generated during electrophoretic runs at higher field strength. The major problems of analytical application of CGE are related to the still insufficient sensitivity of detection of the separated species and the necessity of the generation of various types of gels inside the capillary. The unavoidable shrinking which accompanies the generation of the gel by polymerization and crosslinking within a narrow bore capillary leads to inhomogeneities of the filling. Furthermore the $\zeta$-potential which builds up on the fused-silica surface underneath the gel may extrude a small section of the gel out of the capillary at the cathodic end. Problems of this kind are avoided by a special sequence of surface pretreatment procedures.

An important step of surface modification procedure to be described has been applied before in free zone electrophoresis by Hjerten et al. [S. Hjerten, K. Elenbring, F. Kilar, J.-L. Liao, A. J. C. Chen, C. J. Siebert and M.-D. Zhu, J. Chromatogr., 403 (1987) 47; S. Hjerten, J. Chromatogr., 347 91985) 191] with the aim of elimination of electroosmotic flow and of the avoidance of adsorption of proteins. By this procedure, a non-crosslinked monolayer of polyacrylamide is said to be bonded to the capillary surface.

Already in 1983 Hjerten also filled polyacrylamide gel into glass capillaries of 0.15 mm inner diameter [S. Hjerten, J. Chromatogr., 270 (1983) 1] and could successfully apply such capillaries for the separation of proteins [S. Hjerten, M.-D Zhu, J. Chromatogr., 327 (1985) 157; S. Hjerten K. Elenbring, F. Kilar, J.-L. Liao, A. J. C. Chen, C. J. Siebert and M.-D. Zhu J. Chromatogr., 403 (1987) 47]. In various publications since 1986 Cohen and Karger have shown electrophoretic separations of both classes of biomolecules, proteins and oligonucleotides, which were achieved in gel filled fused silica capillaries. The authors concluded from their experience with the generation and application of such gel capillaries that the gel should be chemically bonded to the capillary surface by treatment of the surface with bifunctional reagents such as 3-methacryloxypropyltrimethoxysilane before the final gel is generated in the capillary [A. S. Cohen and B. L. Karger, J. Chromatogr., 397 (1987) 409; B. L. Karger and A. S. Cohen, Northeastern University, U.S. Pat., U.S. Pat. No. 94 865 706, Oct. 21, 1986; B. L. Karger and A. S. Cohen, Northeastern University, Eur. Pat., EP 324 539 A2, May 1, 1989]. Gel electrophoresis in capillaries can also successfully be performed without pretreatment of the capillary surface [S. Hjerten, J. Chromatogr., 270 (1983) 1]. According to our own experiments, a solution of the acrylamide/bisacylamide mixture can simply be filled into fused-silica capillaries and polymerized either by chemical reagents such as peroxide sulfate or by $\gamma$-rays [J. A. Lux, H.- F. Yin and G. Schomburg, HRC, 13 (1990) 436]. Polymerization of gels on slabs by radiation has been described before [E. I. DuPont de Nemours and Company, Wilmington, Delaware 1989, Eur. Pat., EP OS 0159 694 A2, Oct. 30, 1985]. Gels polymerized in capillaries which are free of bubbles could easily be obtained with $\gamma$-radiation without prior surface treatment [FIG. 1 A; J. A. Lux, H.-F. Yin and G. Schomburg, HRC 13 (1990) 436]. Electropherograms achieved by the authors with gel capillaries which have been manufactured without and with pretreatment of the fused silica surface are compared with regard to resolution and especially peak symmetry [FIG. 2A]. By other authors, gel capillaries obtained without surface pretreatment were found to be insufficiently stable, i.e. their performance was found to decrease rapidly during usage. According to our experience capillaries could be used for as much as 200 measurements without appreciable decrease in performance, provided the gel formation during column production was properly controlled. Only a small section of the gel is likely to be slowly extruded out of the capillary by influence of the electroosmotic flow arising on the untreated surface. By this the separation performance decreases slightly. By occasional cutting off the very first few millimeters of the capillary the separation performance can be restored, however. Decreased lifetimes of gel capillaries caused by such effects have also been reported before (H. Swerdlow and R. Gesteland, Nucleic Acids Research, 18 (1990) 1415].

It appeared to be difficult for other research groups to produce suitable gel capillaries following the procedures described by Cohen and Karger [B. L. Karger and A. S. Cohen, Northeastern University, U.S. Pat., U.S. Pat. No. 94 865 706, Ovy. 21, 1986, B. L. Karger and A. S. Cohen, Northeastern University, Eur. Pat., EP 324 539 A2, May 1, 1989]. Cohen and Karger's method is based on the utilization of a bifunctional compound, for example the well known 3-methacryloxypropyltrimethoxysilane, for surface pretreatment. In this reagent one part of this molecule (i.e. that which contains the three methoxy groups) is intended to effect the chemical bonding to the fused-silica surface while the double bond in the other part of the molecule is available for subsequent copolymerization with acrylamide/bisacrylamide during the formation of the gel. In this way the gel becomes bonded to the fused-silica. According to our trials the unavoidable shrinking of the acrylamide/bisacrylamide mixture during the gel formation by polymerization must take place without any chemical bonding of the gel to the surface, less bubbles arise. By the chemical bonding, sections of the gel under formation are fixed to the surface and prevented from moving unrestrictedly within the capillary during the process of polymerization. The appearance of equidistantly spaced bubbles in the capillary can thus be explained. It has also been tried to generate bubble-free gels, by application of high pressures of up to 400 bar during gel formation generated by means of a HPLC pump [P. F. Bente and J. Myerson, Hewlett-Packard Co., Eur. Pat., EP 272 925 A2, June 29, 1988; U.S. Pat., U.S. Pat. No. 4,810,456, Dec. 24, 1986]. Also, linear hydrophilic polymers such as PEG have been added to the acrylamide/bisacrylamide solution to facilitate the shrinking process of the gel.

Beyond the procedure of gel capillary production described by Cohen and Karger in their patents, we successfully included an additional step of surface pretreatment before the actual gel formation in the capillary is effected. In this step a layer of linear polyacrylamide is generated by starting a polymerization of acrylamide from the vinyl groups which are present on the surface after the pretreatment with the 3-methylacryloxypropyltrimethoxysilane.

IN THE DRAWINGS

The invention will be further described with reference to the accompanying drawings wherein.

Figure 4:
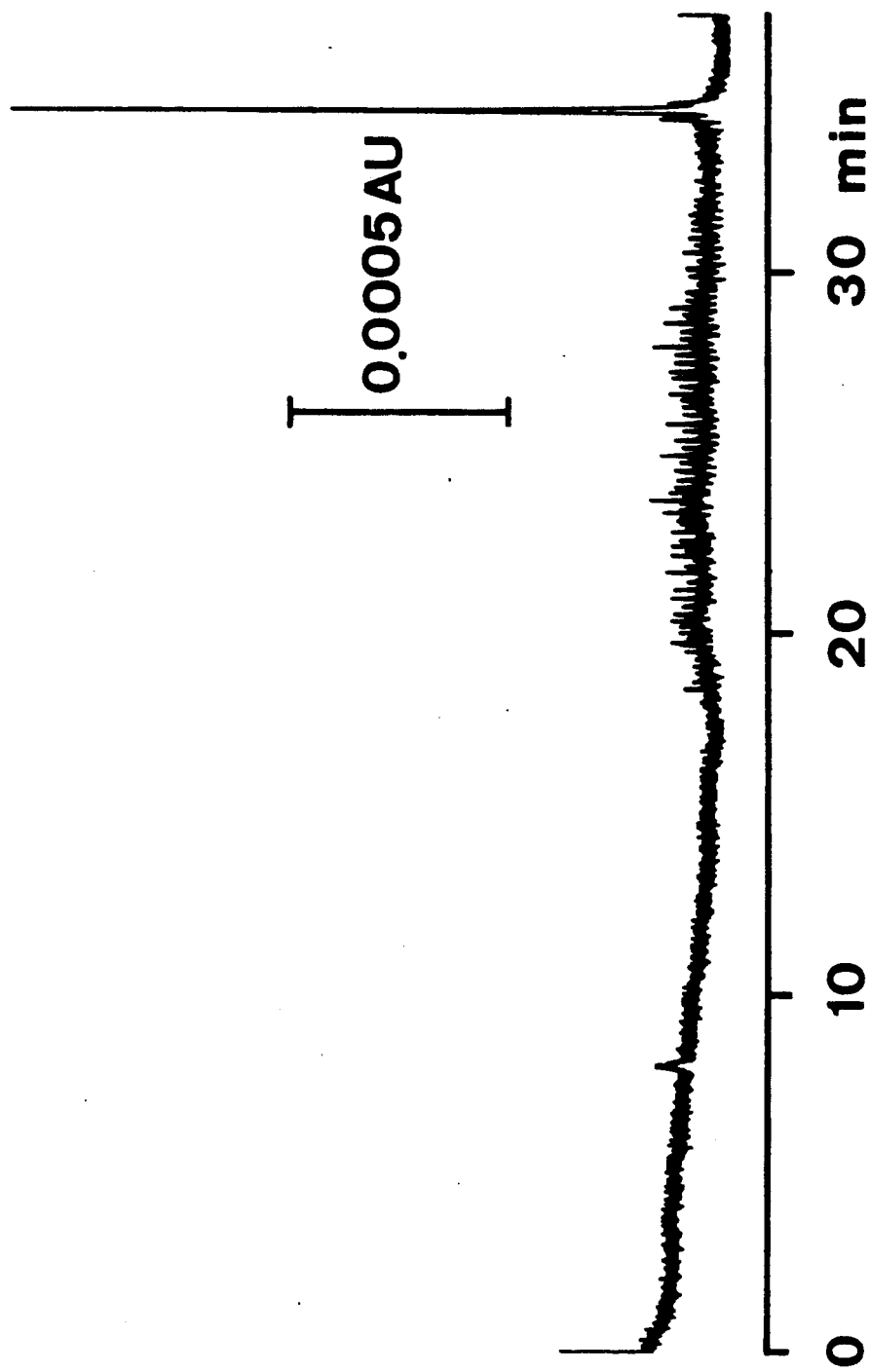

FIG. 4 CGE separation of oligonucleotides (81 mer)

Figure 5:
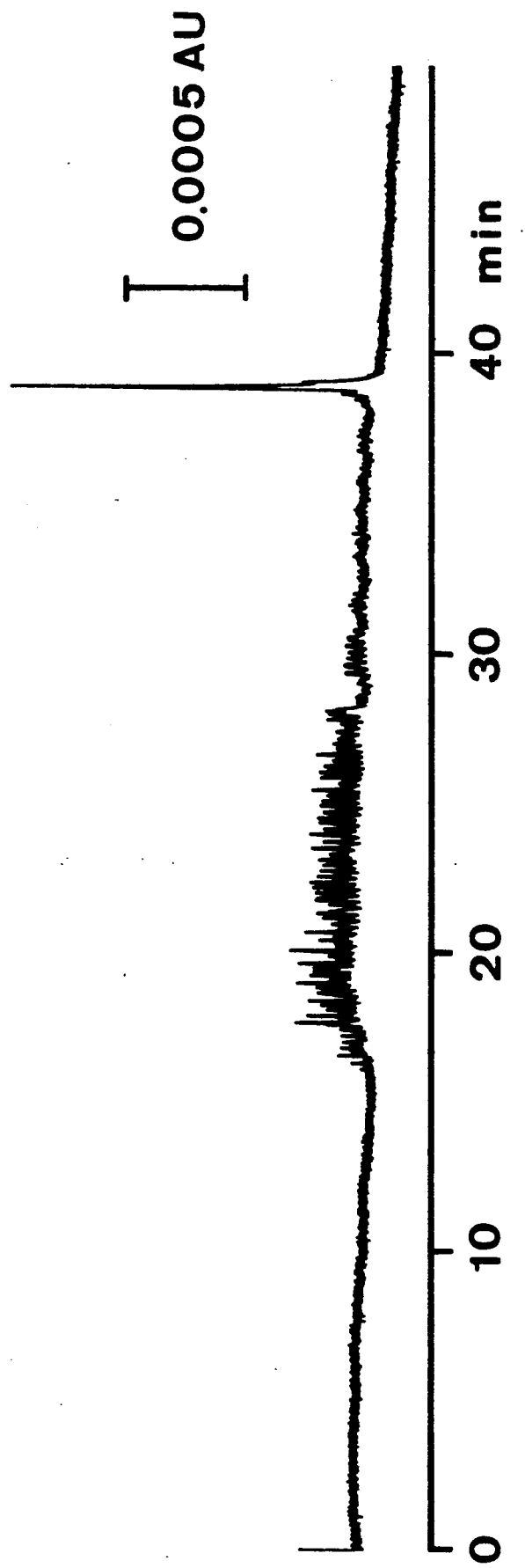
Figures 6A, 6B, 6C, 6D, 6E:
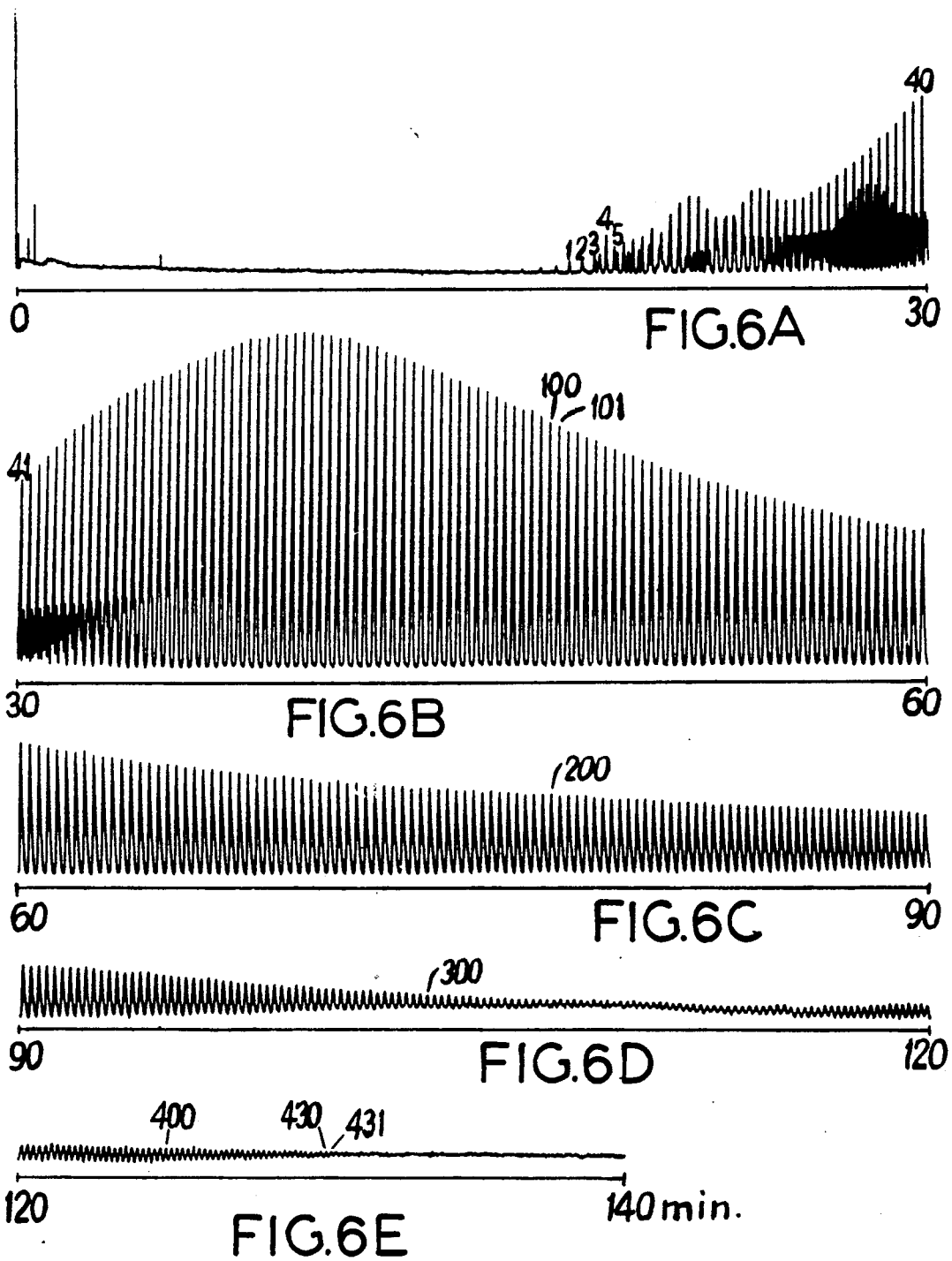

FIG. 5 CGE separation of oligonucleotides (119 mer)

FIG. 6A to 6E are CGE Separation of poly(uridine 5'-phosphate)

Generation of a Coating of Non-Crosslinked Polyacrylamide Before the Introduction of the Acrylamide/Bisacrylamide Solution for the Generation of the Final Gel A non-crosslinked polyacrylamide layer on the capillary surface is provided by rinsing of the capillary with a solution of acrylamide monomer without crosslinker but with a buffer containing the radical initiator.

The non-cross-linked polyacrylamide layer does not impede the shrinking during the subsequent formation of the gel and avoids the formation of bubbles. The build up of a $\zeta$-potential on the surface is also prevented by this linear polyacrylamide layer. In such capillaries therefore the extrusion of gel is avoided. Therefore potentials of up to 400 Volt/cm can be applied to capillaries which have been filled with the cross linked gel after such pretreatment. Moreover, CGE separations with improved resolution and peak symmetry can be performed with gel filled capillaries obtained by a procedure which includes this special step of surface pretreatment. The peak tailing in an electropherogram can be eliminated by the polyacrylamide surface pretreatment.

Generation of Crosslinked Gels in Pretreated Capillaries

A solution containing different acrylamide/bisacrylamide mixtures and a common radical initiator in buffer is introduced into the pretreated capillary under pressure of up to 20 bar. After the crosslinking of the gel is terminated, the capillaries have to be shortly conditioned for the removal of the radical initiator and its reaction products. Then the capillaries are ready for CGE separations.

Figure 1:
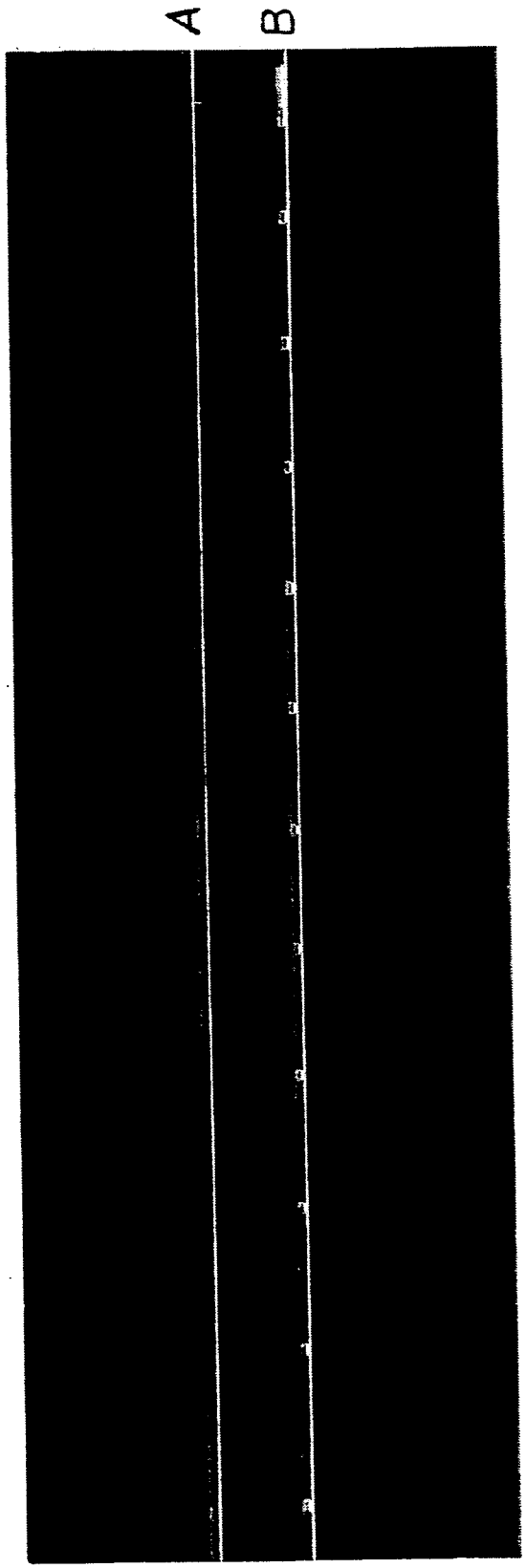
FIG. 1 is a photograph of polyacrylamide gel filled capillaries.
Figures 2A, 2B:
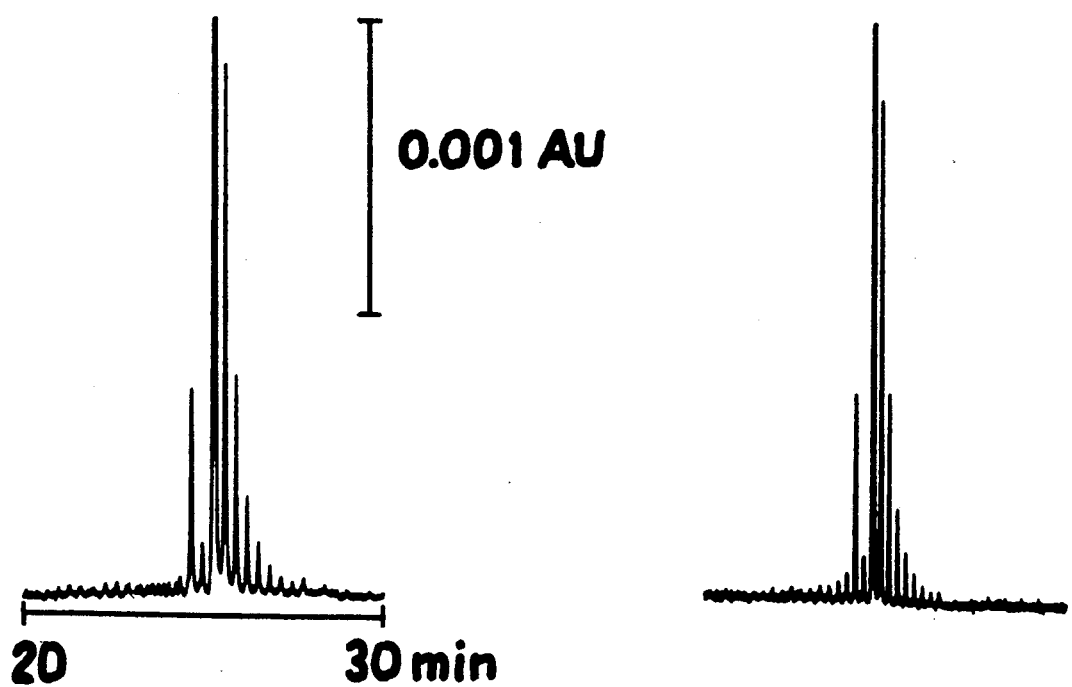
FIGS. 2A and 2B are CGE separation of oligonucleotides (~30-mer)
Figures 3A, 3B:
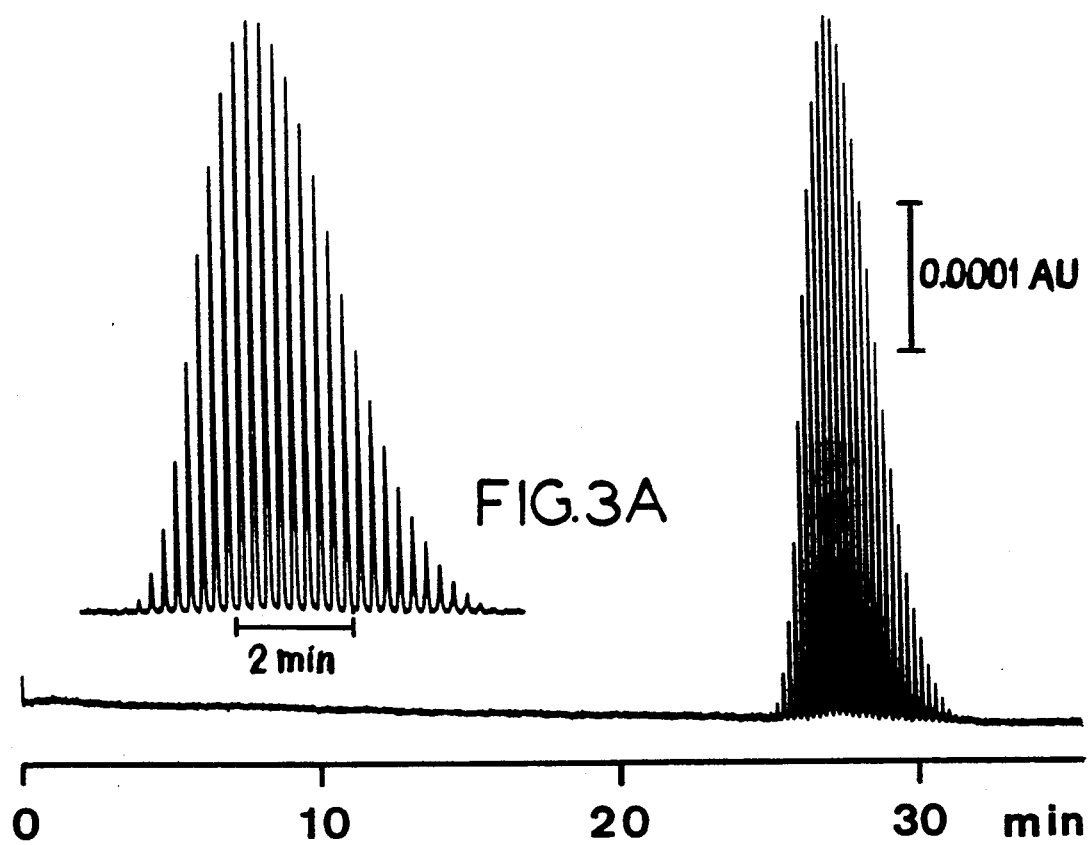
FIGS. 3A and 3B are CGE separation of Polydeoxyadenosine $Pd(A)_{40-60}$

Performance of Separations of Oligonucleotide Samples Using the Gel Capillaries Obtained A typical CGE separation of synthesized oligonucleotides is shown in FIG. 3. The sample contained the series of homologous 40-60 mer polydeoxyadenosines. The peak width at half peak height is determined to be 0.7 mm under these conditions. All the homologues which differ only by one base unit would be completely resolved in a separation of 40 minutes. FIG. 4 and 5 show electropherograms of crude oligonucleotide products directly taken from an oligonucleotide synthesizer. The samples were injected without any pretreatment. The resolution achievable with the capillaries described above is demonstrated by FIG. 6 showing the complete separation of 430 mer poly(uridine 5'-phosphate) from the 431 mer performed in a run of 140 minutes. Even oligomers with higher number of base units can be completely resolved under these conditions and could be visualized with more sensitive detection. Such separations are of interest for analytical DNA sequencing methods.

Capillary gel electrophoretic separations were effected in equipment consisting of a Spectra Physics UV-detector equipped with a capillary holder which contains a spherical lens for focussing of the beam onto the capillary. It also contains the usual grounding and sampling devices with the electrodes. For safety reasons all devices are machined from Perspex and the operator is protected against high voltage by an interlock system. A Vax 3100 work station operates a HCN 35-35000 high voltage power supply (FuG, Rosenheim, FRG) via an optically decoupled FuG Probus III interface and allows voltage control for electromigrative sample introduction as well as the adjustment of the actual separation voltage. Separations were performed in fused silica capillaries (100 $\mu$m o.d., Polymicro Technologies ) of 40-50 cm effective and 50-60 cm total length.

Materials 1.211 g Tris base (Tris[hydroxymethyl]aminomethane, Sigma), 1.546 g boric acid (Aldrich) and 42.04 g urea (Fluka) were dissolved in triply distilled water and diluted to 100 ml. This buffer has pH of 7.6. Samples of oligonucleotides (poly(T), Hoechst AG; poly(A)$_{40-60}$, Pharmacia) were dissolved in that buffer. The acrylamidebisacrylamide stock solution was obtained by dissolving 19.00 g acrylamide (Sigma) and 1.00 g N,N'-methylenebisacrylamide (Fluka) in triply distilled water and diluted to 50 ml.

Detailed Description of the Entire Procedure of the Production of Gel Capillaries The procedures for reproducibly manufacturing a large number of gel columns comprises the following three steps of surface pretreatment:

I. A small section of the outside polyimide coating of the fused silica capillary (Polymicro Technology) is removed to generate windows for UV-detection. The capillary is then leached with 10 ml of 1 M potassium hydroxide solution for three hours at room temperature, and subsequently rinsed with 10 ml distilled water and 10 ml methanol.

II. 20 µl 3-methacryloxypropyltrimethoxysilane (Pentrarch Systems) and 20 µl acetic acid are dissolved in 5 ml methanol. This solution is continuously pumped through the capillary for two hours by pressurizing with nitrogen at room temperature. Then, the capillary is rinsed with 10 ml methanol and 10 ml distilled water.

III. 4 ml 5% acrylamide/water solution and 1 ml 0.05 M Tris base/o.1 M boric acid buffer are mixed and degassed in an ultrasonic bath. 40 µl 10% TEMED (N,N,N',N'-Tetramethylenediamine)/water and 10 µl 10% ammonium persulfate/water (freshly prepared) are added to this acrylamide solution. This final solution is continuously pumped through the capillary for one hour by pressurizing with nitrogen. Then the capillary is flushed with distilled water.

Generation of the Gel in the Capillary

The solution for the generation of gels contains acrylamide/bisacrylamide (6% T, 5% C), 0.1 M Tris, 0.25 M boric acid and 7 M Urea.

5 ml of this solution is carefully degassed in an ultrasonic bath. Then 20-30 µl 10% TEMED, 5-10 µl 10% ammonium persulfate are added to that solution and mixed thoroughly. The final solution is filled into the capillary under nitrogen pressure (20 bar) and polymerized within the capillary under this pressure. At room temperature the polymerization takes 20-30 minutes.

It will be appreciated that the instant specification and claims are set forth by way of illustration and not limitation, and that various modifications and changes may be made without departing from the spirit and scope of the present invention.

What is claimed is:

1. A process for the production of a gel filled silica capillary for electrophoresis, comprising
    a) leaching the capillary with a solution of a basic reagent;
    b) binding a substituted, double bond-containing silane to the silica surface of the capillary;
    c) binding an acrylamide to the treated surface and polymerizing the acrylamide to a linear polyacrylamide, eliminating electroosmotic flow and avoiding chemical bonding of the gel during its subsequent formation; and
    d) contacting the capillary with a solution of acrylamide/bisacrylamide and effecting crosslinking polymerization in the presence of a radical polymerization starter to form a gel.

2. The process according to claim 1, wherein the basic reagent in step (a) comprises potassium hydroxide.

3. The process according to claim 1, wherein the double bond-containing silane comprises 3-methacryloxypropyltrimethoxysilane.

4. A gel filled fused-silica capillary produced by the process of claim 1.

5. In an electrophoresis employing a gel filled fused-silica capillary, the improvement wherein the gel filled fused-silica capillary has been produced by the process of claim 1.

* * * * *

UNITED STATES PATENT AND TRADEMARK OFFICE
CERTIFICATE OF CORRECTION

PATENT NO. : 5,141,612

DATED : August 25, 1992

INVENTOR(S) : Schomburg et al.

It is certified that error appears in the above-identified patent and that said Letters Patent is hereby corrected as shown below:

Title Page & Col 1 line 1    Title [54]: Delete " POLYACRYAMIDE " and substitute -- POLYACRYLAMIDE --

Title Page    [75] Inventors: After " all of " delete " Muml/u/lheim " and substitute -- Mulheim/Ruhr --

Signed and Sealed this

First Day of March, 1994

Attest:

BRUCE LEHMAN

Attesting Officer    Commissioner of Patents and Trademarks